(12) United States Patent
Tang et al.

(10) Patent No.: US 9,857,317 B2
(45) Date of Patent: Jan. 2, 2018

(54) X-RAY FLUOROSCOPIC IMAGING SYSTEM

(71) Applicants: NUCTECH COMPANY LIMITED, Beijing (CN); TSINGHUA UNIVERSITY, Beijing (CN)

(72) Inventors: Huaping Tang, Beijing (CN); Zhiqiang Chen, Beijing (CN); Chuanxiang Tang, Beijing (CN); Huaibi Chen, Beijing (CN); Yuanjing Li, Beijing (CN); Ziran Zhao, Beijing (CN); Yaohong Liu, Beijing (CN); Shangmin Sun, Beijing (CN); Xinshui Yan, Beijing (CN); Zhanfeng Qin, Beijing (CN)

(73) Assignees: NUCTECH COMPANY LIMITED, Beijing (CN); TSINGHUA UNIVERSITY, Beijing (CN)

( * ) Notice: Subject to any disclaimer, the term of this patent is extended or adjusted under 35 U.S.C. 154(b) by 172 days.

(21) Appl. No.: 14/582,069

(22) Filed: Dec. 23, 2014

(65) Prior Publication Data

US 2015/0185166 A1 Jul. 2, 2015

(30) Foreign Application Priority Data

Dec. 30, 2013 (CN) .......................... 2013 1 0742070

(51) Int. Cl.
*G21K 4/00* (2006.01)
*G01N 23/04* (2006.01)
(Continued)

(52) U.S. Cl.
CPC .............. *G01N 23/043* (2013.01); *G01T 7/08* (2013.01); *G01V 5/005* (2013.01); *G01V 5/0033* (2013.01); *G01V 5/0041* (2013.01); *G21K 1/025* (2013.01)

(58) Field of Classification Search
CPC ................. G01N 23/043; G01N 23/04; G01N 2223/419; G01N 23/046; G01N 23/20083;
(Continued)

(56) References Cited

U.S. PATENT DOCUMENTS 4,599,740 A 7/1986 Cable
4,731,807 A * 3/1988 Plessis .................. A61B 6/032
378/146
(Continued)

FOREIGN PATENT DOCUMENTS

CN 2410260 Y 12/2000
CN 2572400 Y 9/2003
(Continued)

OTHER PUBLICATIONS

The extended European search report dated May 29, 2015 in the corresponding European application (14200032.2).

*Primary Examiner* — Irakli Kiknadze
(74) *Attorney, Agent, or Firm* — Kilpatrick Townsend & Stockton LLP

(57) ABSTRACT

The X-ray fluoroscopic imaging system of the present invention comprises: an inspection passage; an electron accelerator; a shielding collimator apparatus comprising a shielding structure, and a first collimator for extracting a low energy planar sector X-ray beam and a second collimator for extracting a high energy planar sector X-ray beam which are disposed within the shielding structure; a low energy detector array for receiving the X-ray beam from the first collimator; and a high energy detector array for receiving the X-ray beam from the second collimator. The first collimator, the low energy detector array and the target point bombarded by the electron beam are located in a first plane; and the second collimator, the high energy detector array and the
(Continued)

target point bombarded by the electron beam are located in a second plane.

18 Claims, 5 Drawing Sheets

(51) Int. Cl.
*G01V 5/00* (2006.01)
*G01T 7/08* (2006.01)
*G21K 1/02* (2006.01)

(58) Field of Classification Search
CPC ...... G01T 7/08; G01V 5/0033; G01V 5/0041; G01V 5/005; G01V 5/0016; G01V 5/0025; G01V 5/0008; G01V 5/0091; G01V 5/00; G01V 5/0058; G01V 5/0066; G01V 5/0069; G01V 5/0075; G21K 1/025; G21K 1/043; H01J 35/00; H01J 23/06; H01J 25/04; H01J 35/14; H01J 3/021; H01J 2235/081; H01J 2235/086; H01J 2235/087; H01J 35/08; H01J 35/30; H01J 37/14; H01J 37/141; H01J 37/147; H01J 37/1472; H01J 37/1475; H01J 2235/166; H01J 2235/06; H01J 2235/16; H01J 35/10; H01J 35/16; H01J 2235/1204; H01J 35/12; A47G 29/124; H02K 5/132; H05G 1/32; H05G 2/00; H05H 7/12; H05H 7/22; H05H 9/04; H05H 9/048
USPC ....... 378/57, 198, 54, 42, 70, 156, 147, 146, 378/158
See application file for complete search history.

(56) References Cited

U.S. PATENT DOCUMENTS

| | | | | |
|---|---|---|---|---|
| 6,628,745 | B1 | 9/2003 | Annis et al. | |
| 6,920,197 | B2* | 7/2005 | Kang | G01V 5/0008 378/198 |
| 7,082,186 | B2* | 7/2006 | Zhao | G01V 5/0016 378/145 |
| 7,302,044 | B2* | 11/2007 | Gabioud | H01J 35/08 378/125 |
| 7,352,843 | B2* | 4/2008 | Hu | G01N 23/04 378/198 |
| 7,957,505 | B1* | 6/2011 | Katz | G01B 15/00 378/147 |
| 2004/0057554 | A1* | 3/2004 | Bjorkholm | G01V 5/0016 378/143 |
| 2006/0008052 | A1 | 1/2006 | Elyan et al. | |
| 2009/0116614 | A1 | 5/2009 | Kotowski et al. | |
| 2010/0119038 | A1 | 5/2010 | Suyama et al. | |
| 2012/0148020 | A1 | 6/2012 | Arroyo, Jr. et al. | |
| 2013/0136230 | A1 | 5/2013 | Arodzero et al. | |

FOREIGN PATENT DOCUMENTS

| | | |
|---|---|---|
| CN | 101358936 A | 2/2009 |
| EP | 2405260 A1 | 1/2012 |
| JP | 63142243 | 6/1988 |
| JP | 01196550 | 8/1989 |
| JP | 2004170393 A | 6/2004 |
| JP | 2005534151 A | 11/2005 |
| JP | 4055743 B2 | 3/2008 |
| JP | 2009036769 A | 2/2009 |
| JP | 2010537163 A | 12/2010 |
| JP | 2011503584 A | 1/2011 |
| WO | 99/09400 A1 | 2/1999 |
| WO | 2004/101162 A2 | 1/2004 |
| WO | 2009/024817 A1 | 2/2009 |
| WO | 2011/091070 A2 | 7/2011 |

* cited by examiner

X-RAY FLUOROSCOPIC IMAGING SYSTEM

CROSS-REFERENCES TO RELATED APPLICATIONS

This application claims priority to Chinese Patent Application No. 201310742070.X, filed on Dec. 30, 2013, entitled "High Energy X-ray Fluoroscopic Imaging System with Double Energies/Double Viewing Angles" by inventors Huaping Tang, Zhiqiang Chen, Chuanxiang Tang, Huaibi Chen, Yuanjing Li, Ziran Zhao, Yaohong Liu, Shangmin Sun, Xinshui Yan and Zhanfeng Qin, which is commonly assigned and incorporated by reference herein for all purposes.

BACKGROUND OF THE INVENTION

Field of the Invention

The present invention relates to a system that performs fluoroscopic imaging on an inspected object from two or more different angles by using an X-ray with two or more different energies respectively, in particular, to a system that performs fluoroscopic imaging by using a high energy X-ray generated by a high energy electron accelerator in nondestructive flaw detection, fluoroscopic imaging, as well as security inspection apparatuses used for large scale container inspection, vehicle inspection, air cargo inspection, train inspection etc.

Description of the Related Art

X-ray is widely used in fields such as industrial nondestructive detection, security inspection etc. For large scale inspected objects, for example, boilers, airspace engines, bulk goods at airports/railways/customs, whole goods of cars/trucks/containers/trains etc., a high energy X-ray, which is generally generated by using an electron accelerator with an energy higher than 2 MeV, is required to be used for their fluoroscopic inspection. The basic method for an electron accelerator to generate an X-ray is as follows: generating an electron beam with an electron gun, accelerating the electron beam with an electric field so that it obtains a high energy, and generating an X-ray by bombarding a target with the high energy electron beam. A high energy X-ray fluoroscopic imaging system utilizes the high-penetration ability of an X-ray. When an X-ray penetrates an inspected object, its intensity will reduce, and the degree of reduction is related to the density, shape, thickness, substance material and the like of the inspected object. The intensity information of the X-ray after penetrating the inspected object is obtained with a detector, and is subjected to processes such as signal processing, algorithm analysis, image reconstruction and the like so as to obtain a fluoroscopic image reflecting the information such as the shape, structure and even the substance material of the inspected object, thereby goals such as structure analysis, flaw inspection, name and type inspection of goods, dangerous goods recognition, prohibited goods inspection and the like are achieved.

Chinese Patent "Method and System for Scanning Radiation Imaging with Double Viewing Angles (Patent No. CN101210895)" discloses a specific method in which two X-ray beams are generated by using one radiation source to perform fluoroscopic imaging on an inspected object and a multi-level image is constructed. This is a low-cost, convenient, and fast deep-recognition method.

Furthermore, Chinese Patent "Multiple Energy Double Frequency Particle Accelerator and Method thereof (Patent No. CN101163372)" discloses a technology that utilizes an electron accelerator to generate electron beams and X-rays with a number of different energies at different time; and Chinese Patents "Apparatus and Method for Generating an X-ray with Different Energies and Material Recognition System (Patent No. CN101076218)", "Method for Radiation Scanning Substance with Multiple Energies and Apparatus thereof (Patent No. CN1995993)", "Method and Apparatus for Substance Recognition (Patent No. CN101435783)" and the like disclose a method in which an inspected object is subjected to fluoroscopic imaging with high energy X-ray and low energy X-ray so as to obtain a fluoroscopic image and materiel information of the inspected object.

Moreover, Chinese Patent "Method and System for Materiel Recognition with Double-Viewing-Angle Multiple-Energy Fluoroscopic Image (Patent No. CN101358936)" discloses a method in which symmetric X-ray beams (with symmetric positions, identical energies, identical intensities etc.) are obtained by two collimators using a multiple energy electron accelerator as the radiation source, thereby a fluoroscopic image with double viewing angles and multiple energies is achieved. This is a combination of the above two types of patent technologies. Here, the multiple energy electron accelerator refers to an accelerator that can output X-rays with different energies at different time, such as the technologies disclosed in Chinese Patents CN101163372 and CN101076218. Although there are two collimators, the X-rays obtained by the two collimators are of the same characteristics.

SUMMARY OF THE INVENTION

To deal with the drawbacks of existing technologies, the present invention obtains two X-ray beams with different characteristics (including different energies, different intensities and different viewing angles) respectively by two collimators at different locations using a low-cost single energy electron accelerator as the radiation source (since the two X-ray beams are generated simultaneously and have different energies, X-ray beams with double energies can be obtained by only a single energy accelerator; and the two X-ray beams both have very good in-plane uniformity), thereby achieves fluoroscopic imaging with double energies/ double viewing angles. The present invention has one or more of the advantages such as low cost, multiple functions, good image quality and the like compared with existing technologies.

The present invention provides an X-ray fluoroscopic imaging system, comprising:

an inspection passage through which an inspected object is passed;

an electron accelerator comprising an electron accelerating unit, an electron emitting unit and a target, the electron beam coming from the electron emitting unit and accelerated by the electron accelerating unit bombarding the target to generate an X-ray;

a shielding collimator apparatus comprising a shielding structure, and a first collimator for extracting a low energy planar sector X-ray beam and a second collimator for extracting a high energy planar sector X-ray beam which are disposed within the shielding structure;

a low energy detector array for receiving the X-ray beam from the first collimator;

a high energy detector array for receiving the X-ray beam from the second collimator;

wherein the shielding structure surrounds the target;

wherein the first collimator, the low energy detector array and the target point bombarded by the electron beam are located in a first plane; and wherein the second collimator, the high energy detector array and the target point bombarded by the electron beam are located in a second plane.

Moreover, in the X-ray fluoroscopic imaging system of the present invention, the angles between the directions in which the first and/or second collimators are disposed and the electron beam bombarding the target are 30° to 150°.

Moreover, in the X-ray fluoroscopic imaging system of the present invention, the angle between the axis of the electron accelerator and the inspection passage is less than 60°.

Moreover, in the X-ray fluoroscopic imaging system of the present invention, the first and second collimators are located on the same side of the axis (L) of the electron beam.

Moreover, in the X-ray fluoroscopic imaging system of the present invention, the axis of the electron accelerator is parallel to the inspection passage.

Moreover, in the X-ray fluoroscopic imaging system of the present invention, the angle between the central symmetric line of the first and second collimators and the inspection passage is larger than 45°.

Moreover, in the X-ray fluoroscopic imaging system of the present invention, the central symmetric line of the first and second collimators is perpendicular to the inspection passage.

Moreover, in the X-ray fluoroscopic imaging system of the present invention, the low and high energy detector arrays are in a linear type arrangement, a segmented linear arrangement, a standard L type arrangement or a C type arrangement, and are constituted by a plurality of low and high energy detectors respectively.

Moreover, in the X-ray fluoroscopic imaging system of the present invention, the low and high energy detector arrays are a plurality of detectors arranged in one row or a plurality of rows respectively.

Moreover, the X-ray fluoroscopic imaging system of the present invention further comprises a signal analyzing and image processing subsystem (7) for receiving signals from the low and high energy detector arrays and generating a fluoroscopic image finally by computation and analysis; and a power supply and control subsystem (6) for providing power and control to the operation of the X-ray fluoroscopic imaging system.

Moreover, the X-ray fluoroscopic imaging system of the present invention further comprises a detector arm support for the mounting and fixation of detectors, wherein the detector arm support is formed into an arrangement structure of linear type, segmented linear type, standard L type or C type.

Moreover, the X-ray fluoroscopic imaging system of the present invention further comprises an adjustable fixing apparatus for fixing the detector arm support on the ground independently.

Moreover, the X-ray fluoroscopic imaging system of the present invention further comprises any combination of the followings: a conveying apparatus for dragging the inspected object to pass through the inspection passage at a given speed; a scatter shielding structure disposed on one side or both sides of the inspection passage; an equipment room for the mounting and fixation of apparatuses such as the electron accelerator and the like; a control room for providing an equipment operation and working place to the working staffs of the system; and a ramp for increasing the height of the inspected object.

Moreover, the X-ray fluoroscopic imaging system of the present invention further comprises a plurality of collimators and a plurality of corresponding detector arrays.

Moreover, in the X-ray fluoroscopic imaging system of the present invention, the electron accelerator is a single energy accelerator, a double energy accelerator or a multiple energy accelerator, and the detector arrays are single energy detector arrays, double energy detector arrays or multiple energy detector arrays correspondingly.

Moreover, the present invention provides a combined and fixed type X-ray fluoroscopic imaging system, comprising:

the X-ray fluoroscopic imaging system according to the present invention;

an equipment room fixed to the ground on one side of the inspection passage and having the electron accelerator and the shielding collimator apparatus mounted therein, the first and second collimators facing the inspection passage at different angles;

a conveying apparatus mounted in the inspection passage;

a first and second detector arm supports disposed on the other side of the inspection passage, fixed to the ground by an adjustable fixing apparatus, and having the low and high energy detector arrays mounted therein respectively;

a scatter shielding structure disposed between the equipment room and the inspection passage; and a control room fixed to the ground, having the signal analyzing and image processing subsystem as well as the power supply and control subsystem mounted therein, and controlling the combined and fixed type X-ray fluoroscopic imaging system.

Moreover, the present invention provides a track moving type X-ray fluoroscopic imaging system, comprising:

the X-ray fluoroscopic imaging system according to the present invention;

a plurality of tracks disposed in parallel, the inspection passage being disposed between two adjacent tracks;

a moving apparatus disposed on the tracks;

an equipment room disposed on the tracks on one side of the inspection passage via the moving apparatus and having the electron accelerator and the shielding collimator apparatus mounted therein, the first and second collimators facing the inspection passage at different angles;

two L type detector arm supports, the "|" segment bottoms thereof being disposed on the tracks on the other side of the inspection passage via the moving apparatus, the other ends being connected and fixed to the top of the equipment room, and the low and high energy detector arrays being mounted therein respectively; and a control room fixed to the ground, having the signal analyzing and image processing subsystem as well as the power supply and control subsystem mounted therein, and controlling the track moving type X-ray fluoroscopic imaging system.

Moreover, the present invention provides a vehicle-mounted moving type X-ray fluoroscopic imaging system, comprising:

the X-ray fluoroscopic imaging system according to the present invention; and a chassis vehicle, and an X-ray source cabin, an equipment cabin, a working cabin, a low energy detector arm support system and a high energy detector arm support system mounted on the chassis vehicle;

wherein the electron accelerator and the shielding collimator apparatus are mounted in the X-ray source cabin, and low and high energy X-ray beams are extracted to one side of the chassis vehicle at different angles through the first and second collimators respectively;

wherein the low energy detector arm support system has the low energy detector array mounted therein, and in a working state, the low energy detector arm support system is opened on one side of the chassis vehicle, forms a "gate" type structure with the chassis vehicle, and makes the low energy detector array locate in the first plane in which the first collimator situates, and in a non-working state, the low energy detector arm support system is folded and stored on the top of the chassis vehicle;

wherein the high energy detector arm support system has the high energy detector array mounted therein, and in a working state, the high energy detector arm support system is opened on one side of the chassis vehicle, forms a "gate" type structure with the chassis vehicle, and makes the high energy detector array locate in the second plane in which the second collimator situates, and in a non-working state, the high energy detector arm support system is folded and stored on the top of the chassis vehicle;

wherein the low and high energy detector arm support systems are located on the same side of the chassis vehicle and form two "gate" type structures one after another with the chassis vehicle, and an internal passage formed by the two "gate" type structures becomes the inspection passage;

wherein the equipment cabin has the power supply and control subsystem as well as the signal analyzing and image processing subsystem mounted therein; and wherein the working cabin has system operation and office equipments mounted therein and controls the vehicle-mounted moving type X-ray fluoroscopic imaging system.

The present invention mainly provides an X-ray fluoroscopic imaging system. The X-ray fluoroscopic imaging system is comprised of a high energy electron accelerator with an energy higher than 2 MeV, a shielding collimator apparatus, an inspection passage, a low energy detector array, a high energy detector array, a power supply and control subsystem, a signal analyzing and image processing subsystem and the like, wherein the electron accelerator and the shielding collimator apparatus generate two groups of X-ray beams with different energies and different angles, the X-ray beams penetrate an inspected object located in the inspection passage and are received by the low energy detector array and the high energy detector array respectively, the received signals are subjected to analyzing process and image reconstruction, and finally a fluoroscopic image reflecting the shape, structure and substance material characteristics of the inspected object is displayed.

The present invention mainly provides an X-ray fluoroscopic imaging system, which performs fluoroscopic imaging by using two groups of X-ray beams with different energies and different angles but with uniform distribution in various directions in their respective planes through a design of the electron accelerator, the shielding collimator apparatus, the low energy detector array, the high energy detector array and various mechanical combining structures. The system has the following advantages: compared with other schemes using a double energy electron accelerator, a single energy electron accelerator is used, thus the structure is simpler and the cost is lower; compared with other schemes generating the high energy and the low energy respectively at different time, the two groups of beams with different energies are generated at the same time, thus the inspection speed is faster; compared with other systems using high and low energy comprehensive detectors, the two groups of X-ray beams with different energies are disposed at different locations with the corresponding detectors being low energy detectors and high energy detectors respectively, thus the structure is simpler and the cost is lower; the intensities of the X-ray beam in various angular directions within the plane are uniform, thus the distance between the radiation source and the inspected object can be shortened and the X-ray can be extracted over a large angle to cover the inspected object; each group of X-ray beams has a plurality of advantages such as small energy spread, uniform intensity distribution and small target size within its planar sector region, thus the image quality of the X-ray fluoroscopic imaging system can be improved. The high energy X-ray fluoroscopic imaging system with double energies/double viewing angles of the present invention can be designed as a specific type such as the fixed type, the combined type, the track moved type, the vehicle-mounted moved type etc., which has advantages such as simple structure, low cost, strong functions, good image quality etc.

DESCRIPTION OF THE EMBODIMENTS

The present invention will be described in details with reference to the drawings hereinafter.

Figure 1:
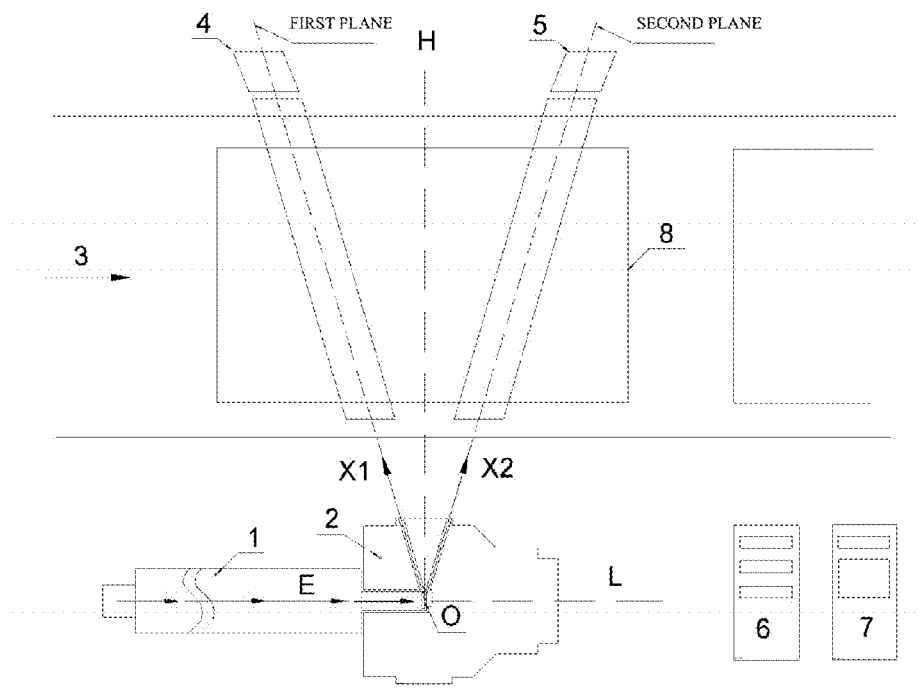
FIG. 1 is a schematic view of the structure of a high energy X-ray fluoroscopic imaging system with double energies/double viewing angles of the present invention.
Figure 2:
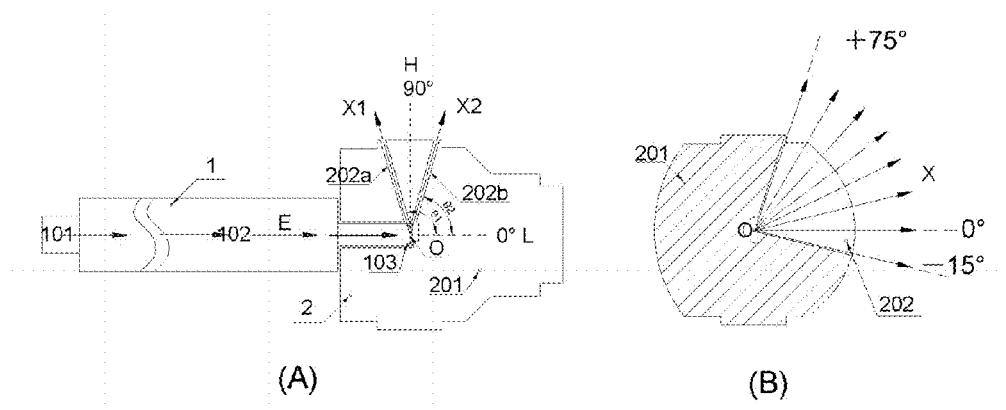
FIG. 2 is a schematic view of the structure of one type of electron accelerator and shielding collimator apparatus of the present invention, wherein (A) is a schematic view of the structure of the electron accelerator and the shielding collimator apparatus, and (B) is a cross-sectional view of the shielding collimator apparatus.

FIG. 1 is a schematic view of the structure of a high energy X-ray fluoroscopic imaging system with double energies/double viewing angles of the present invention. FIG. 2 is a schematic view of the structure of one type of electron accelerator and shielding collimator apparatus of the present invention, wherein (A) is a schematic view of the structure of the electron accelerator and the shielding collimator apparatus, and (B) is a cross-sectional view of the shielding collimator apparatus.

As shown in FIG. 1 and FIG. 2, the high energy X-ray fluoroscopic imaging system with double energies/double viewing angles of the present invention is comprised of a high energy electron accelerator 1, a shielding collimator apparatus 2, an inspection passage 3, a low energy detector array 4, a high energy detector array 5, a power supply and control subsystem 6, and a single analyzing and image processing subsystem 7, wherein the electron accelerator 1 comprises an electron emitting unit 101, an electron accelerating unit 102 and a target 103, and the generated electron beam E has a high energy above 2 MeV; furthermore, the shielding collimator apparatus 2 comprises a shielding structure 201 and at least two collimators 202a, 202b, and the two collimators 202a, 202b are disposed on the same side of the axis of the electron beam E. Furthermore, the collimator 202a, the low energy detector array 4 and the target point bombarded by the electron beam E are located in a first plane, whereas the collimator 202b, the high energy detector array 5 and the target point bombarded by the electron beam E are located in a second plane.

Furthermore, the angles between the first and second planes in which the collimators 202a and 202b are located and the axis of the electron beam E are different, which range from 30° to 150° and from which a high energy X-ray beam and a low energy X-ray beam with uniform distribution of intensity within their respective planes are extracted respectively.

FIG. 1 shows a schematic view of the structure of the high energy X-ray fluoroscopic imaging system with double energies/double viewing angles. The electron accelerator 1 generates a high energy electron beam E, the axis of which is L. The electron beam E bombards a target, and X-ray emitting at 4Π solid angles is generated at the target point location O. The shielding collimator apparatus 2 surrounding the target point O absorbs and shields most X-ray, and a low energy planar sector X-ray beam X1 and a high energy planar sector X-ray beam X2 are extracted respectively by the two collimators 202a and 202b located on the same side of the axis L of the electron beam. X1 and X2 simultaneously penetrate different positions of the inspected object 8 located in the inspection passage 3 at different angles. The X-rays are decreased in intensity by different levels, and are received by the low energy detector array 4 and the high energy detector array 5 respectively. The low energy detector array 4 and the high energy detector array 5 perform preliminary processes on the signals reflecting the X-ray intensities, and thereafter send them to the signal analyzing and image processing subsystem 7. A fluoroscopic image reflecting two sections of the inspected object 8 through which the X-rays penetrate is obtained after processes such as signal analysis, algorithm computation, image construction etc. During operation, if the inspected object 8 and the X-ray fluoroscopic imaging system keep relative motion, that is, respective parts of the inspected object 8 go through the low energy X-ray fluoroscopic region and the high energy X-ray fluoroscopic region sequentially, two complete fluoroscopic images of the inspected object 8 can be obtained, one of which is a low energy left view fluoroscopic image penetrated by the low energy X-ray at the left viewing angle and received by the low energy detector array 4, and the other of which is a high energy right view fluoroscopic image penetrated by the high energy X-ray at the right viewing angle and received by the high energy detector array 5. A comprehensive image with a sense of level is obtained by processing the two images with a double viewing angle image reconstruction algorithm, and an image with materiel characteristics is obtained by processing the two images with a double energy materiel recognition algorithm, finally, these images are combined into a fluoroscopic image of the inspected object 8 with materiel information and level information.

Patent CN101210895 of Nuctech Company Limited describes in detail a method in which fluoroscopic imaging is performed on an inspected object with X-ray beams of two different viewing angles, and a multi-level image is finally constructed. Although the two X-ray beams used in this application are not homogenous (that is, one has low energy and the other has high energy) with more uniform distributions and smaller target points which are different from the symmetric X-rays used in Patent CN101210895, the double viewing angle image reconstruction algorithms can substantially be the same, and thus detailed description is omitted in this application.

Several patents of Nuctech Company Limited, such as CN101435783 and the like, describe in detail a method in which fluoroscopic imaging is performed respectively on an inspected object with X-ray beams of two different energies sequentially, and a fluoroscopic image reflecting the substance materiel information is finally constructed. Although a single energy accelerator is used to generate the low energy and high energy X-rays at two different locations simultaneously in this application, which is different from the method disclosed in Patent CN101435783 and the like in which a double energy accelerator is used to generate respectively the low energy and high energy X-rays at the same position sequentially in time, the methods for substance recognition with double energies are substantially the same, and thus detailed description is omitted in this application.

When the electron beam bombards the target, the intensity and energy distributions of the X-ray beam generated at different azimuth angles relative to the target are different. Therefore, when a plurality of collimators are disposed at different azimuth angles relative to the target, the subsystem comprising the electron accelerator and the shielding collimator apparatus with a plurality of collimators can extract a plurality of groups of X-ray beams with different angles, different intensities and different energy distributions. Moreover, in addition to their different intensities, different energies and different angles, the plurality of groups of X-ray beams as described here have features such as uniform X-ray intensity distribution, small energy spread, small focus size and the like within their respective planar sector regions.

A schematic view of the specific structure of one type of electron accelerator and shielding collimator apparatus used in the present invention is shown in FIG. 2.

The components of the electron accelerator and the shielding collimator apparatus are shown in FIG. 2(A). The electron accelerator 1 is comprised of an electron emitting unit 101, an electron accelerating unit 102 and a target 103. The electron emitting unit 101 generates an electron beam E. The electron accelerating unit 102 accelerates the electron beam E to be a high energy electron beam with an axis of the electron beam being L, which is also defined as the axis of the electron accelerator 1. The high energy electron beam bombards the target, and X-rays emitting to respective angles in the space are generated at the target point location O. The shielding collimator apparatus 2 surrounds the target, and is comprised of a shielding structure 201 and collimators 202. The collimators 202 are planar sector slits disposed in the shielding structure 201, and are used for extracting X-rays to be used and limiting the X-rays in required planar shapes. The corner point of the sector is the target point O bombarded by the electron beam, and the thickness of the slit is in the millimeter order, which is generally, for example, 0.5 mm to 5 mm, typically is 2 mm. Moreover, the slit may also be a gap with a certain conicity, for example, the thickness of the gap is thinner at positions closer to the target point location O, and the thickness of the gap is thicker at positions further from the target point location O. For example, the gap thickness at the target point is 1.5 mm, the thickness of the middle segment is 2 mm, and the thickness at the gap outlet is 2.5 mm. There are two collimators 202 in the structure shown in FIG. 2, namely, 202a and 202b. For convenience of description, sometimes, the collimator 202a is referred to as the first collimator and the collimator 202b is referred to as the second collimator in this application. The deflection angle θ1 between the collimator 202a and the electron beam is larger, and the extracted planar sector low energy X-ray beam is referred to as X1; the deflection angle θ2 between the collimator 202b and the electron beam is smaller, and the extracted planar sector high energy X-ray beam is referred to as X2. The central line between the X-ray beams X1 and X2, i.e., the central symmetric line of the collimator 202a and 202b, is defined as H. The angle between H and L is 90° in FIG. 2, which is a recommended design structure with better effects.

A cross-sectional view of one type of shielding collimator apparatus 2 is shown in FIG. 2(B). The shielding collimator apparatus 2 surrounds the target point O, and most of the X-rays generated at the target point are shielded and absorbed by the shielding structure 201, and planar sector X-ray beams can only be extracted from the gaps of the collimators 202. The thicknesses of the gaps, the sizes of the field angles and the locations of the openings determine the shape distributions of the planar sector X-ray beams. Typically as shown in FIG. 2(B), as for the X-ray beam, its thickness is 2 mm, and the total field angle is 90°, wherein the downward field angle is 15° (−15°) and the upward field angle is 75° (+75°) with reference to the horizontal plane (0°).

In the present invention, the angle between the axis L of the electron accelerator 1 and the inspection passage 3 is smaller than 60°, and it is recommended that they are parallel. A case in which the axis L of the electron accelerator 1 and the inspection passage 3 form an angle β is shown in FIG. 3(A).

In the present invention, the angle between the central symmetric line of the two collimators 202a, 202b and the inspection passage 3 is larger than 45°, and it is recommended that they are perpendicular. A case in which the central symmetric line H of the collimators 202a, 202b and the inspection passage 3 form an angle γ is shown in FIG. 3(B).

Figure 3:
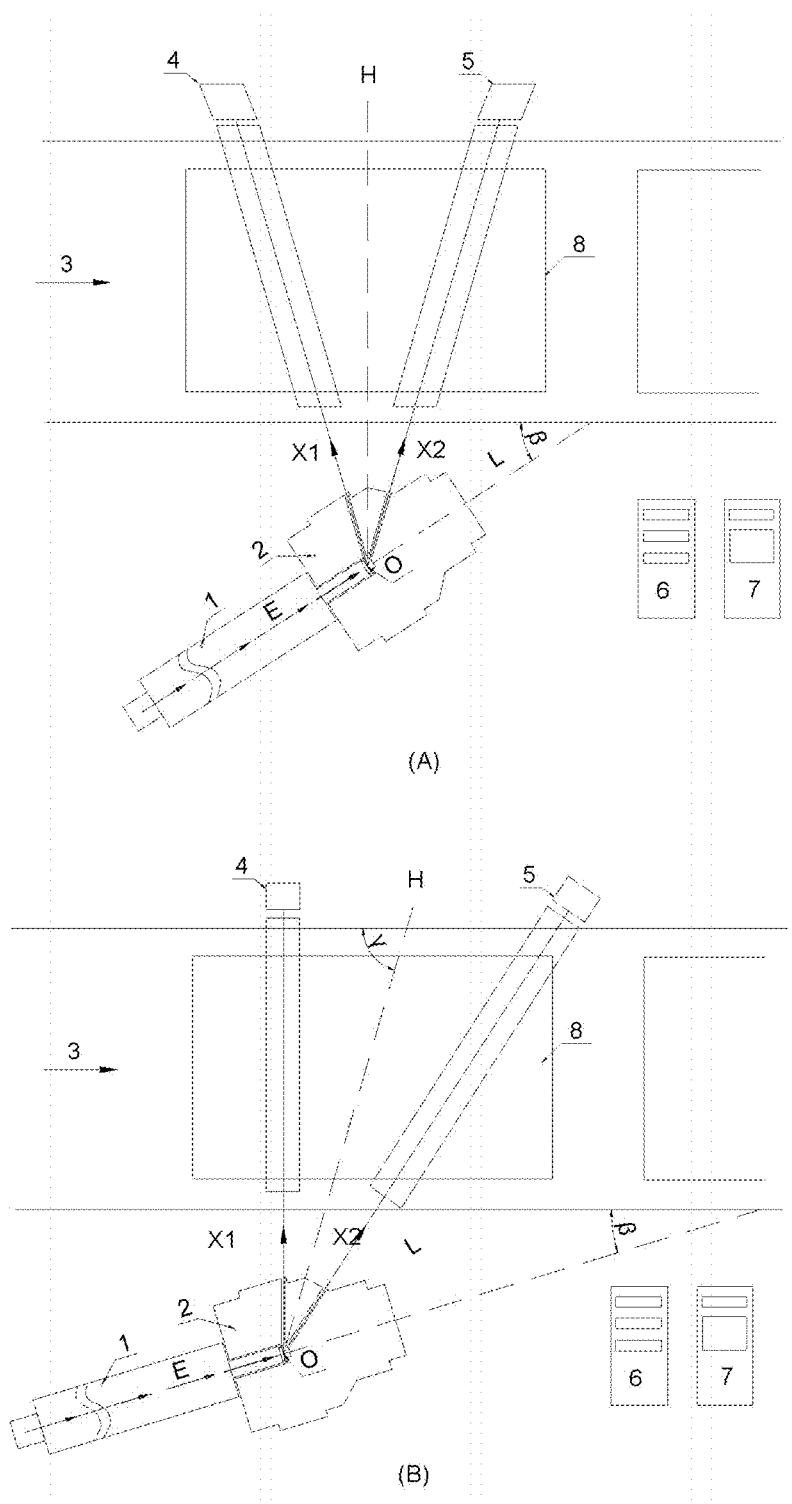
FIG. 3 is schematic views of the structures of another two types of high energy X-ray fluoroscopic imaging systems with double energies/double viewing angles, wherein (A) illustrates a case in which the axis L of the electron accelerator and the inspection passage 3 form an angle $\beta$, and (B) illustrates a case in which the central symmetric line H of collimators 202a and 202b and the inspection passage 3 form an angle $\gamma$.

Schematic views of the structures of another two types of high energy X-ray fluoroscopic imaging systems with double energies/double viewing angles are shown in FIG. 3.

FIG. 3(A) shows the structure of an X-ray fluoroscopic imaging system in which the axis L of the electron accelerator 1 and the inspection passage 3 form an angle β. In the case β is smaller than 60°, the X-ray fluoroscopic imaging system can achieve the function of double energies/double viewing angles as long as the deflection angle θ1 between the collimator 202a and the electron beam as well as the deflection angle θ2 between the collimator 202b and the electron beam are adjusted to proper angles. However, as the angle β gets bigger, the energy difference between the low energy X-ray X1 and the high energy X-ray X2 will be affected. Thus, it is recommended that β=0, i.e., the axis L of the electron accelerator 1 is parallel to the inspection passage 3.

FIG. 3(B) shows the structure of an X-ray fluoroscopic imaging system in which the central symmetric line H of the two collimators 202a, 202b and the inspection passage 3 form an angle γ. In the case γ is larger than 45°, the X-ray fluoroscopic imaging system can achieve the function of double energies/double viewing angles well as long as the deflection angle θ1 between the collimator 202a and the electron beam as well as the deflection angle θ2 between the collimator 202b and the electron beam are adjusted to proper angles. However, as the angle γ gets smaller, the path of the high energy X-ray X2 gets longer. On one hand, this will increase the number of detectors so as to increase the cost; on the other hand, this will make the viewing angle too skew, and will affect the level effect of a reconstructed image. Therefore, it is recommended that γ is about 90°, for example, the central symmetric line H of the two collimators 202a, 202b is perpendicular to the inspection passage 3.

In the present invention, the low energy detector array 4 and the high energy detector array 5 are in a linear type arrangement, a segmented linear type arrangement, a standard L type arrangement or a C type arrangement, and are constituted by a plurality of low energy or high energy detectors.

In the present invention, the low energy detector array 4 and the high energy detector array 5 are a plurality of detectors arranged in one row or a plurality of rows.

Figure 4:
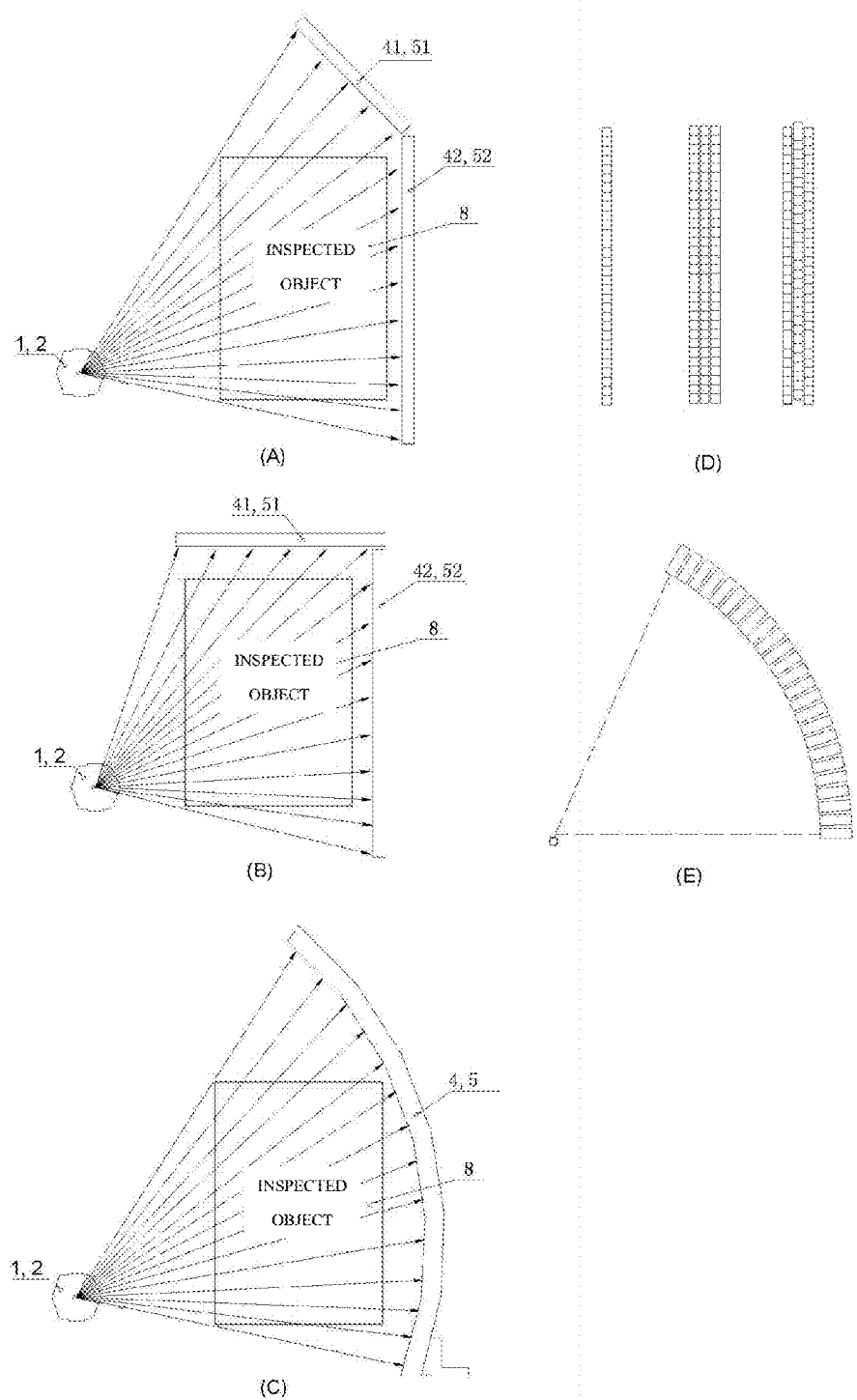
FIG. 4 is schematic views of the structures and arranging methods of several detector arrays with different shapes, wherein (A) illustrates the segmented linear type, (B) illustrates the standard L type, (C) illustrates the C type, (D) illustrates detectors in single line and in multiple lines, and (E) illustrates a case in which the end planes of the detectors point at the target point O.

Different shapes and different arranging methods of several types of detector arrays are shown in FIG. 4.

FIG. 4(A) shows a case in which the detector array is arranged in a segmented linear manner. The low energy detector array 4 is divided into two linear segments, i.e., a top low energy detector array 41 and a side low energy detector array 42; likewise, the high energy detector array 5 is divided into a top high energy detector array 51 and a side high energy detector array 52. X-rays generated from the target point O are extracted into a planar sector low energy X-ray beam and a planar sector high energy X-ray beam by two collimators (in the drawing, perpendicular to the paper plane and overlapping each other), which penetrate the inspected object 8 and are received by the low energy detector array 4 and the high energy detector array 5 respectively. The sector regions formed by the detector arrays and the target point O can cover the cross-sections of the inspected object 8 completely. A detector array in such a configuration has a simple structure and is easy to be mounted and fixed.

FIG. 4(B) shows a case in which the detector array is arranged in a standard L type manner. The low energy detector array 4 is divided into two linear segments perpendicular to each other, i.e., a low energy detector array 41 located at the top "-" segment and a low energy detector array 42 located at the side "|" segment; likewise, the high energy detector array 5 is divided into a high energy detector array 51 located at the top "-" segment and a high energy detector array 52 located at the side "|" segment. X-rays generated from the target point O are extracted into a planar sector low energy X-ray beam and a planar sector high energy X-ray beam by two collimators (in the drawing, perpendicular to the paper plane and overlapping each other), which penetrate the inspected object 8 and are received by the low energy detector array 4 and the high energy detector array 5 respectively. The sector regions formed by the detector arrays and the target point O can cover the cross-sections of the inspected object 8 completely. A detector array in such a configuration has a simple and regular structure, and is easy to be formed into a collapsible structure.

FIG. 4(C) shows a case in which the detector array is arranged in a C type manner. The low energy detector array 4 and the high energy detector array 5 are located on two arc segments respectively, and the centers of the arc segments are the target point location O. X-rays generated from the target point O are extracted into a planar sector low energy X-ray beam and a planar sector high energy X-ray beam by two collimators (in the drawing, perpendicular to the paper plane and overlapping each other), which penetrate the inspected object 8 and are received by the low energy detector array 4 and the high energy detector array 5 respectively. The sector regions formed by the detector arrays and the target point O can cover the cross-sections of the inspected object 8 completely. In a detector array in such a configuration, the distances between respective detectors and the target point are the same, and the intensity of an X-ray beam extracted by the collimator of the present invention is uniformly distributed at respective angles, therefore, the intensities of the original X-ray signals received by respective detectors are uniform, and thus detectors with completely uniform amplifications can be chosen to form a detector array, which helps to simplify the system and reduce the cost.

FIG. 4(D) shows a case in which the arranging manner of detectors is observed from the X-ray direction. The detector array may be a plurality of detectors arranged in one row, or may be a plurality of detectors arranged in a plurality of rows. When detectors are arranged in a plurality of rows, the relative positions of the detectors may be either juxtaposed or staggered. The use of a plurality of rows of detectors may increase the cost of detectors, however, the slice thickness of the inspected object obtained every time is multiplicative, and the inspection speed of the system can be improved multiplicatively.

FIG. 4(E) shows that the end planes of detectors at respective positions are all perpendicular to the X-ray. In an X-ray fluoroscopic imaging system, all detectors generally receive the incidence of the X-ray with front faces, i.e., all detectors are disposed such that their end planes point to the target point O.

One type of high energy X-ray fluoroscopic imaging system with double energies/double viewing angles of the present invention also comprises a detector arm support 9 for the mounting and fixation of detectors and for the forming of an arrangement structure of the linear type, the segmented linear type, the standard L type or the C type. The detector arm support 9 is generally tubular, and can protect the detectors mounted therein. Openings are disposed at positions corresponding to the end planes of the detectors so that X-ray may reach the end planes of the detectors directly without being influenced.

One type of high energy X-ray fluoroscopic imaging system with double energies/double viewing angles of the present invention also comprises a conveying apparatus 10 for dragging the inspected object 8 to pass through the inspection passage at a given speed. The conveying apparatus may use various conveying means such as belts, rollers, chains, wheels, towbars etc.

One type of high energy X-ray fluoroscopic imaging system with double energies/double viewing angles of the present invention also comprises an adjustable fixing apparatus 11 for fixing the detector arm support 9 on the ground independently and for adjusting the position and the directions of the openings of the detector arm support 9 flexibly.

One type of high energy X-ray fluoroscopic imaging system with double energies/double viewing angles of the present invention also comprises scatter shielding structure(s) disposed on one side or both sides of the inspection passage 3 for shielding reflected rays and scattered rays generated when the X-ray penetrates the inspected object 8 so as to guarantee the safety of the working staffs and the public. The scatter shielding structure on the side of the collimators has strip-shaped openings at positions corresponding to the collimators to allow X-ray beams pass therethrough; the scatter shielding structure on the side of the detectors is located behind the detector arm support.

One type of high energy X-ray fluoroscopic imaging system with double energies/double viewing angles of the present invention also comprises an equipment room for the mounting and fixation of apparatuses such as the electron accelerator 1 and the like. The equipment room provides working environment with suitable temperature and humidity so as to meet related national regulations on the operation and management of X-ray apparatuses. The equipment room may be various cabins such as an equipment cabin transformed from a container, or a temporary room or a fixed building.

One type of high energy X-ray fluoroscopic imaging system with double energies/double viewing angles of the present invention also comprises a control room for providing the staffs of the system with a suitable place for equipment operation and working. The control room may be various cabins such as an equipment cabin transformed from a container, or a temporary room or a fixed building.

One type of high energy X-ray fluoroscopic imaging system with double energies/double viewing angles of the present invention also comprises a ramp for raising the height of the inspected object so that every part of the inspected object can be within the covering ranges of the low energy X-ray and the high energy X-ray.

It should be particularly noted that, in one type of X-ray fluoroscopic imaging system of the present invention, the collimators may be located either on the same side or on different sides of the axis of the electron beam.

It should be particularly noted that, in one type of X-ray fluoroscopic imaging system of the present invention, the low energy detectors and the high energy detectors mean that the X-ray beams they receive are of low energy and high energy relatively, but the detectors themselves do not necessarily have obvious differences. It is recommended that the low energy detectors and the high energy detectors are detectors having better detection results on X-ray beams with relatively low energy and X-ray beams with relatively high energy respectively.

It should be particularly noted that, in one type of X-ray fluoroscopic imaging system of the present invention, the shielding collimator apparatus 2 may have more collimators on the same side of the electron beam so as to form a high energy X-ray fluoroscopic imaging system with more energies and more viewing angles.

It should be particularly noted that, in one type of X-ray fluoroscopic imaging system of the present invention, the electron accelerator 1 may be a single energy accelerator or a pulse-alternating multiple energy accelerator. When the electron accelerator 1 has double (multiple) energies, the corresponding detectors are double (multiple) energy detectors.

It should be particularly noted that, in one type of X-ray fluoroscopic imaging system of the present invention, respective components may be completely arranged on the ground so as to form a fixed type system; alternatively, a part of the components may be fixed on the ground and another part of the components may be arranged on a short-distance moving apparatus so as to form a partial moving type system; still alternatively, respective components may be completely arranged on a long-distance moving apparatus so as to form a moving type system.

Figure 5:
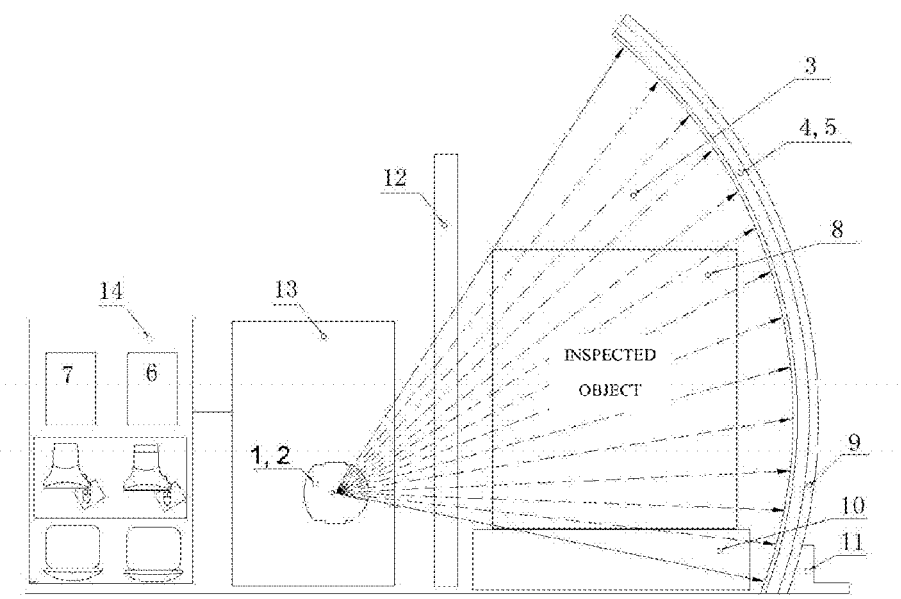
FIG. 5 is a schematic view of the structure of a combined and fixed type high energy X-ray fluoroscopic imaging system with double energies/double viewing angles.

Moreover, an example of a combined and fixed type high energy X-ray fluoroscopic imaging system with double energies/double viewing angles is shown in FIG. 5.

The combined and fixed type high energy X-ray fluoroscopic imaging system with double energies/double viewing angles shown in FIG. 5 is comprised of an electron accelerator 1, a shielding collimator apparatus 2, an inspection passage 3, a low energy detector array 4, a high energy detector array 5, a power supply and control subsystem 6, a signal analyzing and image processing subsystem 7, detector arm supports 9, a conveying apparatus 10, adjustable fixing apparatuses 11, a scatter shielding structure 12, an equipment room 13 and a control room 14.

The electron accelerator 1, the shielding collimator apparatus 2 and the like are mounted in the equipment room 13 and are located on one side of the inspection passage 3. The axis of the electron accelerator 1 is parallel to the inspection passage 3, and the collimators 202a and 202b face the inspection passage 3 and the central symmetric line thereof is perpendicular to the inspection passage 3. The total field angles of the sector slits of the collimators 202a and 202b are 90°, wherein the downward field angles are −15°, whereas the upward field angles are +75°. The distance between the electron accelerator 1 and the inspection passage 3 is small, and a large scale inspected object 8 can also be covered, thereby the region occupied by the system is reduced. The C type detector arm supports 9 are located on the other side of the inspection passage 3. The C type detector arm supports 9 have two groups with the low energy detector array 4 and the high energy detector array 5 mounted therein respectively, which are fixed on the ground by the adjustable fixing apparatuses 11 and which are located on positions corresponding to the collimators 202a and 202b respectively. That is, the target point location O, the collimator 202a and the low energy detector array 4 are located within a first plane, whereas the target point location O, the collimator 202b and the high energy detector array 5 are located with a second plane. A planar roller type conveying apparatus 10 is mounted in the inspection passage 3, which can carry large scale cases such as air containers, air trays and the like while they pass through the X-ray inspection region. The scatter shielding structure 12 is disposed between the equipment room 13 and the inspection passage 3, and is a composite structure of a lead plate and a steel plate, wherein the lead plate is used for shielding the X-ray and the steel plate is used for structural supporting and fixation. The scatter shielding structure 12 is provided with strip-shaped openings at positions corresponding to the collimators 202a and 202b, and will not block the low energy X-ray X1 and the high energy X-ray X2. The power supply and control subsystem 6, the signal analyzing and image processing subsystem 7, office equipments and the like are arranged in the control room 14. The equipment room 13 and the control room 14 are steel-structured cabins with heat insulation layers, which are equipped with basic facilities such as windows, doors, air conditioners, illumination apparatuses, ventilation apparatuses and the like; moreover, they have lifting structures on the top and fixing structures on the bottom, and thus can be disposed and mounted flexibly. The equipment room, the control room, the conveying apparatus and the detector arm supports are connected via electrical cables, and respective components are independent relatively and can be fixed and mounted flexibly on site, therefore, this is referred to as a combined and fixed type. This combined and fixed type high energy X-ray fluoroscopic imaging system with double energies/double viewing angles is suitable for performing fluoroscopic imaging inspection on inspected objects such as large scale and medium scale containers, cases for centralized luggage shipping and the like at places such as airports, freight stations and the like.

Figure 6:
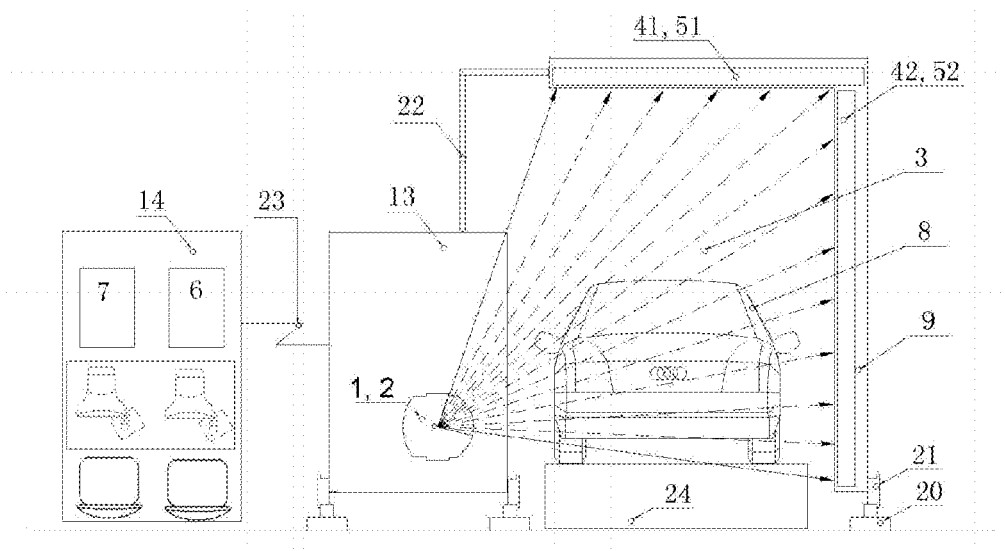
FIG. 6 is a schematic view of the structure of a track moved type high energy X-ray fluoroscopic imaging system with double energies/double viewing angles.

An example of a track moving type high energy X-ray fluoroscopic imaging system with double energies/double viewing angles is shown in FIG. 6.

The track moving type high energy X-ray fluoroscopic imaging system with double energies/double viewing angles shown in FIG. 6 is comprised of an electron accelerator 1, a shielding collimator apparatus 2, an inspection passage 3, a low energy detector array 4, a high energy detector array 5, a power supply and control subsystem 6, a signal analyzing and image processing subsystem 7, L type detector arm supports 9, an equipment room 13, a control room 14, tracks 20, moving apparatuses 21, connecting and supporting structures 22, an electrical connecting structure 23 and the like.

The electron accelerator 1, the shielding collimator apparatus 2 and the like are mounted in the equipment room 13, which is disposed on the tracks 20 fixed to the ground via the moving apparatus 21 on the bottom of the equipment room 13, and are located on one side of the inspection passage 3. The axis of the electron accelerator 1 is parallel to the inspection passage 3. The collimators 202a and 202b face the inspection passage 3 and the central symmetric line thereof is perpendicular to the inspection passage 3. One end (the "-" segment) of each of two groups of L type detector arm supports 9 is connected and fixed to the top of the equipment room 13 via the connecting and supporting structure 22, and the other end (the bottom of the "|" segment) of each of the two groups of L type detector arm supports 9 is disposed on the track 20 on the other side of the inspection passage 3 via the moving apparatus 21. Respective tracks are parallel to each other, and the detector arm supports 9 and the equipment room 13 form gate structures disposed on a plurality of parallel tracks. Respective moving apparatuses can be implemented in a plurality of ways such as wheels driven by a stepping motor etc., and keep synchronous motions so that the "gate" structures formed by the detector arm supports 9 and the equipment room 13 move on the tracks as a whole. The low energy detector array 41 and the high energy detector array 51 are mounted respectively within the top "-" segments of the two groups of L type detector arm supports 9, and the low energy detector array 42 and the high energy detector array 52 are mounted respectively within the side "|" segments thereof. The target point location O, the collimator 202a, the low energy detector array 41 and the low energy detector array 42 are located within a first plane, whereas the target point location O, the collimator 202b, the high energy detector array 51 and the high energy detector array 52 are located within a second plane. The power supply and control subsystem 6, the signal analyzing and image processing subsystem 7, office equipments and the like are arranged in the control room 14. The control room 14 is fixed to the ground and is connected to the equipment room 13 via the electrical connecting structure, The electrical connecting structure comprises cables and an apparatus for automatically retracting and releasing the cables, such as an automatic winding roll for cable and the like, which can retract and release the cables automatically and adjust the lengths of the cables flexibly during moving of the equipment room 13 on the tracks. This type of high energy X-ray fluoroscopic imaging system with double energies/double viewing angles is partially fixed to the ground and partially arranged on the tracks, and can move back and forth within a certain distance, thus is referred to as a track moving type.

The fluoroscopic imaging process performed on an inspected object by a track moving type high energy X-ray fluoroscopic imaging system with double energies/double viewing angles is as follows. The inspected object 8 parks on the inspection passage 3. The electron accelerator 1 starts to work and generates X-ray beams X1 and X2 together with the shielding collimator apparatus 2. At the same time, the "gate" structures formed by the equipment room 13 and the detector arm supports 9 move from one end to the other end of the tracks at a given speed so that the planar sector low energy X-ray X1 extracted by the collimator 202a and the planar sector high energy X-ray X2 extracted by the collimator 202b sweep the inspected object parked on the inspection passage 3 sequentially and are received by the low energy detector array 4 and the high energy detector array 5 respectively. Finally, a fluoroscopic image reflecting the multi-level structure and the material information of the inspected object is generated by the signal analyzing and image processing subsystem 7.

The track moving type high energy X-ray fluoroscopic imaging system with double energies/double viewing angles can also comprise a ramp 24 for raising the height of the inspected object 8 so as to achieve complete imaging of the inspected object 8. For example, during the inspection of a car, the tires may be imaged together so as to check whether there is prohibited goods such as drugs and the like in the tires. The ramp 24 has a known design structure, such as a steel-frame structure and the like. During imaging of the system, the structural information on a part of the ramp is blanked so as to alleviate the influence of the ramp on the image of the inspected object 8.

The track moving type high energy X-ray fluoroscopic imaging system with double energies/double viewing angles may be arranged at places such as customs, land ports, important locations and the like to perform fluoroscopic imaging on medium and small trucks, various towed carriages, various cars, small passenger cars and the like so as to obtain clear fluoroscopic images. Also, it has the functions of multi-level display and material recognition. Therefore, the inspection on smuggled goods, dangerous goods and prohibited goods can be accomplished well.

Figure 7:
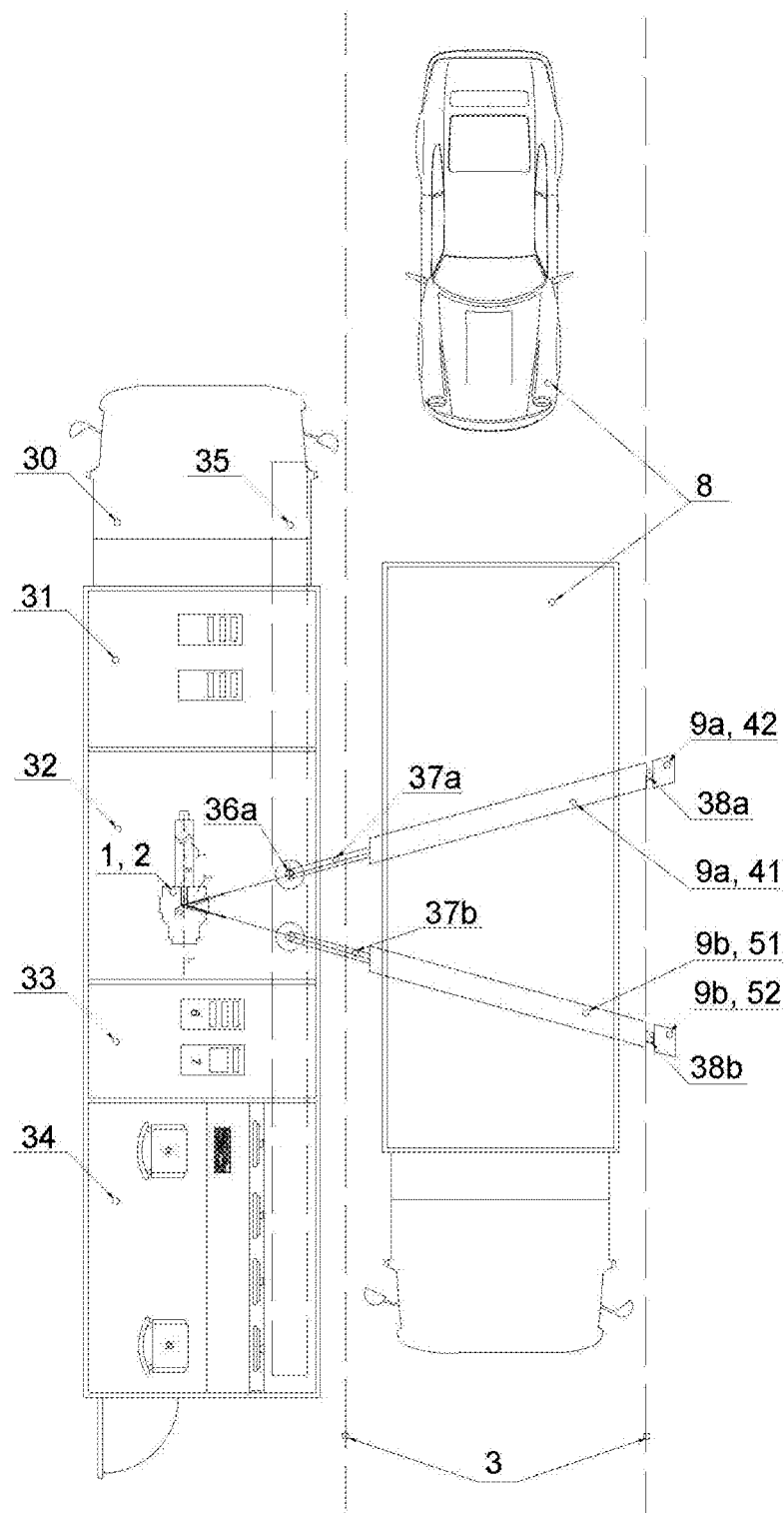
FIG. 7 is a schematic view of the structure of a vehicle-mounted moved type high energy X-ray fluoroscopic imaging system with double energies/double viewing angles.

Moreover, an example of a vehicle-mounted moving type high energy X-ray fluoroscopic imaging system with double energies/double viewing angles is shown in FIG. 7.

The vehicle-mounted moving type high energy X-ray fluoroscopic imaging system with double energies/double viewing angles shown in FIG. 7 is comprised of an electron accelerator 1, a shielding collimator apparatus 2, an inspection passage 3, a low energy detector array 4, a high energy detector array 5, a power supply and control subsystem 6, a signal analyzing and image processing subsystem 7, collapsible L type detector arm supports 9 (two, 9a and 9b respectively), a chassis vehicle 30, a power supply cabin 31, an X-ray source cabin 32, an equipment cabin 33, a working cabin 34, elevating and rotating apparatuses 36 (two, 36a and 36b respectively), connecting and supporting apparatuses 37 (two, 37a and 37b respectively), collapsible connecting apparatuses 38 (two, 38a and 38b respectively).

The chassis vehicle 30 is a large scale truck, such as a Volvo triple axis heavy duty chassis vehicle. A plurality of cabins are provided thereon, which are the power supply cabin 31, the X-ray source cabin 32, the equipment cabin 33, the working cabin 34 and the like. Each cabin is equipped with facilities such as heat insulation layers, windows, doors, air conditioners, illumination apparatuses, ventilation apparatuses and the like as needed.

Power supply equipments are mounted in the power supply cabin 31, which may be power generating equipments such as diesel generators, and/or commercial power connecting apparatuses such as equipments able to be connected to the commercial power including cables and automatic winding rolls. The power supply cabin supplies power for the whole system, and generally has a power capacity above 15 kVA.

The electron accelerator 1 and the shielding collimator apparatus 2 are mounted in the X-ray source cabin 32. The axis L of the electron accelerator 1 is parallel to the left and right symmetric line of the chassis vehicle 30. The central symmetric line H of the two collimators 202a and 202b of the shielding collimator apparatus 2 is perpendicular to the left and right symmetric line of the chassis vehicle. The low energy X-ray X1 and the high energy X-ray X2 extracted emit from the same side of the chassis vehicle 30 via strip-shaped openings at the side of the X-ray source cabin 32. The vehicle-mounted moving type high energy X-ray fluoroscopic imaging system with double energies/double viewing angles further comprises a radiation safety protection subsystem, which is comprised of apparatuses such as auxiliary shielding equipments, radiation signs, sound and light alarms, environmental dose monitors, video monitors, safety chains and the like according to related national regulations. All the apparatuses or part of the apparatuses of the radiation safety protection subsystem are mounted in the X-ray source cabin, too.

The power supply and control subsystem 6, the signal analyzing and image processing subsystem 7 and other related apparatuses are mounted in the equipment cabin 33. The power supply and control subsystem 6 further comprises a lower-level subsystem for controlling the movement of the detector arm support system.

The working cabin 34 is mounted at the end of the chassis vehicle 30. Office tables and chairs, display apparatuses, operation and control apparatuses and the like are mounted therein. It is a place where the working staffs operate the vehicle-mounted moving type high energy X-ray fluoroscopic imaging system with double energies/double viewing angles.

The elevating and rotating apparatuses 36 are mounted on the top of the X-ray source cabin 32. The collapsible L type detector arm supports 9 are connected to the elevating and rotating apparatuses 36 via the connecting and supporting apparatuses 37; also, each of the collapsible L type detector arm supports 9 is divided into two linear segments of "-" and "|", which are connected via the collapsible connecting apparatus 38 at their joint point. These apparatuses are collectively referred to as the detector arm support system. The elevating and rotating apparatuses 36 are used for the elevation and the rotation of a certain angle of the detector arm support system with respect to the chassis vehicle, and can be implemented in plurality of ways, such as by employing hydraulic apparatuses, pneumatic apparatuses, motors or the like. The collapsible connecting apparatuses 38 are used for the connection of the two linear segments "-" and "|" of the L type detector arm supports 9 as well as for folding these two segments into a "=" shape or stretching them into an "L" shape in specific states, and can also be implemented in plurality of ways, such as by employing hydraulic link lever apparatuses, pneumatic link lever apparatuses, motor and gear combination apparatuses or the like.

Corresponding to the two collimators 202a, 202b and the two groups of X-ray beams (i.e., the low energy X1 and the high energy X2), the elevating and rotating apparatuses 36, the connecting and supporting apparatuses 37, the collapsible L type detector arm supports 9 and the collapsible connecting apparatuses 38 are also divided into two groups with substantially the same structures and functions respectively, namely, 36a and 36b, 37a and 37b, 9a and 9b, 38a and 38b. The detailed connecting relations among them are as follows: (a) at a position corresponding to the collimator 202a, the elevating and rotating apparatus 36a is mounted on the top of the X-ray source cabin 32; the collapsible L type detector arm support 9a is connected to the elevating and rotating apparatus 36a via the connecting and supporting apparatus 37a; the collapsible L type detector arm support 9a is divided into two linear segments of "-" and "|", wherein the low energy detector array 41 is mounted in the "-" segment, the low energy detector array 42 is mounted in the "|" segment, and the two segments are connected via the collapsible connecting apparatus 38a at their joint point; this part is referred to as the low energy detector arm support system; (b) at a position corresponding to the collimator 202b, the elevating and rotating apparatus 36b is mounted on the top of the X-ray source cabin 32; the collapsible L type detector arm support 9b is connected to the elevating and rotating apparatus 36b via the connecting and supporting apparatus 37b; the collapsible L type detector arm support 9b is divided into two linear segments of "-" and "|", wherein the high energy detector array 51 is mounted in the "-" segment, the high energy detector array 52 is mounted in the "|" segment, and the two segments are connected via the collapsible connecting apparatus 38b at their joint point; this part is referred to as the high energy detector arm support system.

All apparatuses of the vehicle-mounted moving type high energy X-ray fluoroscopic imaging system with double energies/double viewing angles are integrated on one chassis vehicle, forming a special equipment vehicle. Generally, the detector arm support systems are folded and placed in the region at position 35 (as illustrated by the dashed box in FIG. 7). The vehicle-mounted moving type high energy X-ray fluoroscopic imaging system with double energies/double viewing angles can be driven on various roads such as country highways and those with higher levels through the chassis vehicle, thereby can meet application requirements in all occasions flexibly.

Working Principle and Process

The vehicle-mounted moving type high energy X-ray fluoroscopic imaging system with double energies/double viewing angles is driven to a certain place with application requirement, and its detailed working process is as follows.

(1) The vehicle-mounted moving type high energy X-ray fluoroscopic imaging system with double energies/double viewing angles is parked at a flat and open working place, the working staffs enter the working cabin, and the system is started.

(2) The power supply apparatuses in the power supply cabin 31 start to work, e.g., generators start, or electrical cables are connected to commercial power supplying equipments, and the vehicle-mounted moving type high energy X-ray fluoroscopic imaging system with double energies/double viewing angles obtains power supply.

(3) The lower-level subsystem for controlling the movement of the detector arm support system of the power supply and control subsystem 6 operates so that: (a) the elevating and rotating apparatus 36a is first elevated to a certain height and then is rotated a certain angle clockwise so that the low energy detector array 41 and the low energy detector array 42 are located in the first plane where the target point location O and the collimator 202a are located; the collapsible connecting apparatus 38a drives the collapsible L type detector arm support 9a to stretch from the folded "=" state to the "L" state; (b) the elevating and rotating apparatus 36b is first elevated to a certain height and then is rotated a certain angle counter-clockwise so that the high energy detector array 51 and the high energy detector array 52 are located in the second plane where the target point location O and the collimator 202b are located; the collapsible connecting apparatus 38b drives the collapsible L type detector arm support 9b to stretch from the folded "=" state to the "L" state; (a) and (b) may be performed sequentially or simultaneously. The detector arm support system on one side of the chassis vehicle forms a "gate" type structure with the chassis vehicle, and the passage inside the "gate" type structure is the inspection passage 3, as shown by the dashed lines in FIG. 7.

(4) Inspected objects, e.g., container trucks, vans, passenger cars, small cars and the like, are parked on the inspection passage in a queue, and persons such as drivers and the like leave the inspected objects.

(5) The power supply and control subsystem 6 starts the electron accelerator 1, and outputs a low energy sector X-ray beam X1 in a first plane via the collimator 202a and a high energy sector X-ray beam X2 in a second plane via the collimator 202b at the same time. X1 reaches, directly or after penetrating the inspected object, the low energy detector array 41 located in the "-" segment of the detector arm support 9a and the low energy detector array 42 located in the "|" segment thereof; X2 reaches, directly or after penetrating the inspected object, the high energy detector array 51 located in the "-" segment of the detector arm support 9b and the high energy detector array 52 located in the "|" segment thereof. All detector arrays convert the received signals and then transmit them to the signal analyzing and image processing subsystem 7.

(6) While the power supply and control subsystem 6 starts the electron accelerator, it starts the auto-driving of the chassis vehicle to travel along a straight line at a given speed so that the X-ray beams X1 and X2 sweep all the inspected objects on the inspection passage sequentially.

(7) The signal analyzing and image processing subsystem 7 obtains the low energy X-ray fluoroscopic data and the high energy X-ray fluoroscopic data reflecting the geometric structures and material information of the inspected objects synchronously (synchronously with (5), (6) described above), generates fluoroscopic images of the inspected objects with multi-level information and material information after processes such as signal analysis, algorithm calculation, image construction and the like, and displays them on the display apparatuses in real time. The working staffs accomplish inspection tasks such as smuggled goods inspection, dangerous goods inspection, prohibited goods inspection and the like based on the image information.

(8) The inspected objects, e.g., container trucks, vans, passenger cars, small cars and the like, drive away from the inspection passage after the inspection is finished and when no problems need to be dealt with.

(9) If there exist multi-batch inspected objects, the above (4)~(8) are repeated. And, if the inspection work ends, the electron accelerator 1 is stopped so as to stop the generation of X-rays, and: (a) the collapsible connecting apparatus 38a first drives the collapsible L type detector arm support 9a to retract from the opened "L" state into the folded "=" state; the elevating and rotating apparatus 36a is rotated a certain angle counter-clockwise to make the folded L type detector arm support 9a position above the dashed box region 35, and then is dropped for a certain height to reach the storage place; (b) the collapsible connecting apparatus 38b first drives the collapsible L type detector arm support 9b to retract from the opened "L" state into the folded "=" state; the elevating and rotating apparatus 36b is rotated a certain angle clockwise to make the folded L type detector arm support 9b position above the dashed box region 35, and then is dropped for a certain height to reach the storage place; (a) and (b) may be performed sequentially or simultaneously.

(10) The working staffs stop the system, turn off the power supply, leave the working cabin, and may drive the vehicle-mounted moving type high energy X-ray fluoroscopic imaging system with double energies/double viewing angles to the next working place.

The vehicle-mounted moving type high energy X-ray fluoroscopic imaging system with double energies/double viewing angles may be arranged at places such as customs, land ports, airports, important locations and the like to perform fluoroscopic imaging on container vehicles, large, medium and small trucks, various cars, small passenger cars and the like so as to obtain clear fluoroscopic images. Also, it has the functions of multi-level identification and material recognition. Therefore, the inspection on smuggled goods, dangerous goods and prohibited goods can be accomplished well.

Beneficial Effects

The present invention mainly provides an X-ray fluoroscopic imaging system, which performs fluoroscopic imaging by using two groups of X-ray beams with different energies and different angles but with uniform distribution in various directions in their respective planes through a design of the electron accelerator, the shielding collimator apparatus, the low energy detector array, the high energy detector array and various mechanical combining structures. The system has the following advantages: compared with other schemes using a double energy electron accelerator, a single energy electron accelerator is used, thus the structure is simpler and the cost is lower; compared with other schemes generating the high energy and the low energy respectively at different time, the two groups of beams with different energies are generated at the same time, thus the inspection speed is faster; compared with other systems using high and low energy comprehensive detectors, the two groups of X-ray beams with different energies are disposed at different locations with the corresponding detectors being low energy detectors and high energy detectors respectively, thus the structure is simpler and the cost is lower; the intensities of the X-ray beam in various angular directions within the plane are uniform, thus the distance between the radiation source and the inspected object can be shortened and the X-ray can be extracted over a large angle to cover the inspected object; each group of X-ray beams has a plurality of advantages such as small energy spread, uniform intensity distribution and small target size within its planar sector region, thus the image quality of the X-ray fluoroscopic imaging system can be improved. The high energy X-ray fluoroscopic imaging system with double energies/double viewing angles of the present invention can be designed as a specific type such as the fixed type, the combined type, the track moving type, the vehicle-mounted moving type etc., which has advantages such as simple structure, low cost, strong functions, good image quality etc.

What is claimed is:

1. An X-ray fluoroscopic imaging system, comprising:
   an inspection passage (3) through which an inspected object (8) is passed;
   an electron accelerator (1) comprising an electron accelerating unit (102), an electron emitting unit (101) and a target (103), an electron beam (E) coming from the electron emitting unit and accelerated by the electron accelerating unit bombarding the target to generate an X-ray, wherein the X-ray has different energy distributions at different azimuth angles relative to the target (103);
   a shielding collimator apparatus (2) comprising a shielding structure (201), and a first collimator (202a) for extracting a low energy planar sector X-ray beam and a second collimator (202b) for extracting a high energy planar sector X-ray beam which are disposed within the shielding structure;
   a low energy detector array (4) for receiving the X-ray beam from the first collimator;
   a high energy detector array (5) for receiving the X-ray beam from the second collimator;
   wherein the shielding structure surrounds the target;
   wherein the first collimator, the low energy detector array and a target point (O) bombarded by the electron beam are located in a first plane; and
   wherein the second collimator, the high energy detector array and the target point bombarded by the electron beam are located in a second plane.

2. The X-ray fluoroscopic imaging system according to claim 1, wherein the angles between the directions in which the first and/or second collimators are disposed and the electron beam bombarding the target are 30° to 150°.

3. The X-ray fluoroscopic imaging system according to claim 1, wherein the angle between the axis of the electron accelerator and the inspection passage is less than 60°.

4. The X-ray fluoroscopic imaging system according to claim 1, wherein the first and second collimators are located on the same side of the axis (L) of the electron beam.

5. The X-ray fluoroscopic imaging system according to claim 1, wherein the axis of the electron accelerator is parallel to the inspection passage.

6. The X-ray fluoroscopic imaging system according to claim 1, wherein the angle between the central symmetric line of the first and second collimators and the inspection passage is larger than 45°.

7. The X-ray fluoroscopic imaging system according to claim 1, wherein the central symmetric line of the first and second collimators is perpendicular to the inspection passage.

8. The X-ray fluoroscopic imaging system according to claim 1, wherein the low and high energy detector arrays are in a linear type arrangement, a segmented linear arrangement, a standard L type arrangement or a C type arrangement, and are constituted by a plurality of low and high energy detectors respectively.

9. The X-ray fluoroscopic imaging system according to claim 1, wherein the low and high energy detector arrays are a plurality of detectors arranged in one row or a plurality of rows respectively.

10. The X-ray fluoroscopic imaging system according to claim 1, further comprising:
    a signal analyzing and image processing subsystem (7) for receiving signals from the low and high energy detector arrays and generating a fluoroscopic image finally by computation and analysis; and a power supply and control subsystem (6) for providing power and control to the operation of the X-ray fluoroscopic imaging system.

11. The X-ray fluoroscopic imaging system according to claim 1, further comprising:
a detector arm support (9) for the mounting and fixation of detectors, the detector arm support being formed into an arrangement structure of linear type, segmented linear type, standard L type or C type.

12. The X-ray fluoroscopic imaging system according to claim 11, further comprising:
an adjustable fixing apparatus (11) for fixing the detector arm support on the ground independently.

13. The X-ray fluoroscopic imaging system according to claim 1, further comprising any combination of the followings:
a conveying apparatus (10) for dragging the inspected object to pass through the inspection passage at a given speed;
a scatter shielding structure (12) disposed on one side or both sides of the inspection passage;
an equipment room (13) for the mounting and fixation of apparatuses such as the electron accelerator and the like;
a control room (14) for providing an equipment operation and working place to the working staffs of the system; and
a ramp (24) for increasing the height of the inspected object.

14. The X-ray fluoroscopic imaging system according to claim 1, comprising a plurality of collimators and a plurality of corresponding detector arrays.

15. The X-ray fluoroscopic imaging system according to claim 1, wherein the electron accelerator is a single energy accelerator, a double energy accelerator or a multiple energy accelerator, and the detector arrays are single energy detector arrays, double energy detector arrays or multiple energy detector arrays correspondingly.

16. A combined and fixed type X-ray fluoroscopic imaging system, comprising:
the X-ray fluoroscopic imaging system according to claim 1;
an equipment room (13) fixed to the ground on one side of the inspection passage and having the electron accelerator and the shielding collimator apparatus mounted therein, the first and second collimators facing the inspection passage at different angles;
a conveying apparatus (10) mounted in the inspection passage;
a first and second detector arm supports (9) disposed on the other side of the inspection passage, fixed to the ground by an adjustable fixing apparatus, and having the low and high energy detector arrays mounted therein respectively;
a scatter shielding structure (12) disposed between the equipment room and the inspection passage; and
a control room (14) fixed to the ground, having the signal analyzing and image processing subsystem as well as the power supply and control subsystem mounted therein, and controlling the combined and fixed type X-ray fluoroscopic imaging system.

17. A track moving type X-ray fluoroscopic imaging system, comprising:
the X-ray fluoroscopic imaging system according to claim 1;

a plurality of tracks (20) disposed in parallel, the inspection passage being disposed between two adjacent tracks;
a moving apparatus (21) disposed on the tracks;
an equipment room (13) disposed on the tracks on one side of the inspection passage via the moving apparatus and having the electron accelerator and the shielding collimator apparatus mounted therein, the first and second collimators facing the inspection passage at different angles;
two L type detector arm supports (9), a vertical segment bottoms thereof being disposed on the tracks on the other side of the inspection passage via the moving apparatus, the other ends being connected and fixed to the top of the equipment room, and the low and high energy detector arrays being mounted therein respectively; and
a control room (14) fixed to the ground, having the signal analyzing and image processing subsystem as well as the power supply and control subsystem mounted therein, and controlling the track moving type X-ray fluoroscopic imaging system.

18. A vehicle-mounted moving type X-ray fluoroscopic imaging system, comprising:
the X-ray fluoroscopic imaging system according to claim 1; and
a chassis vehicle (30), and an X-ray source cabin (32), an equipment cabin (33), a working cabin (34), a low energy detector arm support system and a high energy detector arm support system mounted on the chassis vehicle;
wherein the electron accelerator and the shielding collimator apparatus are mounted in the X-ray source cabin, and low and high energy X-ray beams are extracted to one side of the chassis vehicle at different angles through the first and second collimators respectively;
wherein the low energy detector arm support system has the low energy detector array mounted therein, and in a working state, the low energy detector arm support system is opened on one side of the chassis vehicle, forms a "gate" type structure with the chassis vehicle, and makes the low energy detector array locate in the first plane in which the first collimator situates, and in a non-working state, the low energy detector arm support system is folded and stored on the top of the chassis vehicle;
wherein the high energy detector arm support system has the high energy detector array mounted therein, and in a working state, the high energy detector arm support system is opened on one side of the chassis vehicle, forms a "gate" type structure with the chassis vehicle, and makes the high energy detector array locate in the second plane in which the second collimator situates, and in a non-working state, the high energy detector arm support system is folded and stored on the top of the chassis vehicle;
wherein the low and high energy detector arm support systems are located on the same side of the chassis vehicle and form two "gate" type structures one after another with the chassis vehicle, and an internal passage formed by the two "gate" type structures becomes the inspection passage;
wherein the equipment cabin has the power supply and control subsystem as well as the signal analyzing and image processing subsystem mounted therein; and wherein the working cabin has system operation and office equipments mounted therein and controls the vehicle-mounted moving type X-ray fluoroscopic imaging system.

* * * * *